United States Patent [19]
Mühlemann et al.

[11] 4,208,795
[45] Jun. 24, 1980

[54] METHOD OF PROVIDING A LIVING PERSON'S BODY WITH INFORMATION FOR FORENSIC IDENTIFICATION

[76] Inventors: Hans R. Mühlemann, Beustweg 8, Zürich; Ernesto Steiner, Bachtelweg 26, Egg; Marco Brandestini, Streulistrasse 39, Zürich, all of Switzerland

[21] Appl. No.: 886,439

[22] Filed: Mar. 14, 1978

[30] Foreign Application Priority Data

Mar. 22, 1977 [CH] Switzerland ............... 3588/77

[51] Int. Cl.² .................................................. A61C 5/08
[52] U.S. Cl. .................................... 433/203; 433/226
[58] Field of Search ........................... 32/15, 2, 1, 12

[56] References Cited

U.S. PATENT DOCUMENTS

4,027,391  6/1977  Samis ........................ 32/15

Primary Examiner—Robert Peshock
Attorney, Agent, or Firm—Frishauf, Holtz, Goodman & Woodward

[57] ABSTRACT

An identification plate of gold alloy is inserted in a small blind hole drilled into the crown of a tooth. The hole is then filled with a durable filler which hardens around the plate to embed it in a durable, heat resistant filling. The filling material can be colored so that it is readily located when identification is desired. For making the identification, the filler is dissolved away to leave the plate, which can be read by means of optical magnification.

Also disclosed is an electrical device especially adapted for providing plate blanks with the desired identifying information.

9 Claims, 3 Drawing Figures

METHOD OF PROVIDING A LIVING PERSON'S BODY WITH INFORMATION FOR FORENSIC IDENTIFICATION

BACKGROUND OF THE INVENTION

The present invention relates to identifying markings for the purpose of forensic identification. The identification subject is a human being, the identification carrier a tooth of the human being, and the identification mark an information carrier of metal, organic or inorganic polymers, glass, porcelain or similar durable materials.

Every year more than 1,000 people are killed in aircraft crashes alone (SAMIS, P. L.—Systems of Dental Identification; Can. Soc. Forensic Sci. J. 8:77–86, 1975). In Switzerland alone 3,500 people died in all types of accidents in 1976 (Swiss Statistical Yearbook 1976). The same number of persons are determined to be missing in a single year in the Glasgow area (BUTLER, O. H.—Unidentified Bodies and Missing Persons Circulation of Dental Data for Identification; J. Forensic Soc. 14:223–224, 1974). In single earthquakes thousands of people can be killed and, large numbers of victims must also be expected in train crashes, floods, etc. The accurate identification of the victims is necessary for a number of reasons, including considerations relating to insurance, inheritance, and religion.

Over the past few decades, the development of identification methods has been largely limited to establishing methods for identifying living persons. For example, various anatomical marks on living humans and their changes on the corpse have been described, together with their postmortem applicability by comparison with the in vivo findings. Virtually no practically relevant advances have been made with comparative methods other than finger printing.

There are at least seven different methods for the identification of a corpse (GUSTAFSON, G.—Forensic Odontology; Staples Press, London, G.B. 1966, LUNTZ, L. L. & LUNTZ, P.—Handbook for Dental Identification, Lippincott Co., Philadelphia, U.S.A., 1973; MIDDA, M.—The Role of Dental Identification in Mass Disasters, J. Irish Dent. Ass. 20:67–69, 1974). These are:

1. Visual Identification

Identification of the corpse by relative or acquaintances using photographs of either the facial or other physical features. The prerequisite for this is that the body features such as shape, colour, etc. still exist on the corpse.

2. Identification by items of clothing

Analysis of the chemical compositon of clothing textiles, identifying labels, etc. The prerequisite for this is the existance of clothing and possibly proof to the effect that they belong to the corpse. p 3. Identification by Passport Comparison of the passport and other documents on the corpse and other documents with photographs which are normally kept in files.

4. Identification by jewelry

Identification by relatives or acquaintances, possibly with the aid of photographs or documents relative to jewelry. The prerequisite for this is that the jewels used for identification purposes actually belonged to the corpse.

5. Identification by finger prints

Comparison of the finger-prints before and after death. The prerequisite is the existance of antemortem finger-prints.

6. Identification by Medical and Dental investigations

Comparison of medical and dental documents which existed prior to death with specific postmortem features. Here again the prerequisite is the existence of relatively stable antemortem documents.

7. Identification by exclusion

Forensic science has always attached great importance to teeth as an identification object because they fulfil the following requirements;

(a) Durability: Paleontological investigations have shown that after death the teeth are the best preserved parts of the entire skeleton (TELLIER, L., DANHIEZ, P. SALAUM, M.—Identification des Cadavres à Partir des Fichiers Dentaires; Rev. Stomatoodontol. Nord. Fr. 28:268–276, 1973).

(b) Heat Resistance: Statistics reveal that even in severly mutilating fires, teeth suffer relatively little damage.

(c) Versatility: the 32 teeth have complex anatomical features making it possible to easily differenciate them or compare them.

The use of only one of the above methods is seldom sufficient for a completely satisfactory identification of a corpse. Often additional clarifications are required to obtain comparative data.

In addition, much is left to be desired with respect to the reliability of these methods, particularly in cases where there are insufficient points of agreement. In addition, it is generally necessary to have a large team of specialists for an often difficult and complicated identification. Frequently no such experts are available, so that further difficulties can result due to irreversible errors during the identification procedure.

Of the 605 victims of various aircraft crashes the above methods were able to identify 577 corpses, and of these almost half, i.e. 260 only by dental experts (MIDDA, 1974).

Using the conventional comparative identification procedure, an average five hours per corpse were necessary (SAMIS, 1975), provided that antemortem X-ray photographs or dental charts existed and could be discovered. However, even with this very time-consuming comparative procedure, reliable identification was frequently not possible.

Up to now the forensic dentist has exclusively used the four-stage system of LUNTZ & LUNTZ, 1973 for the identification of bodies.

(a) Examination of the oral cavity of the corpse.

(b) Documentation of specific features on the corpse.

(c) Obtaining antemortem comparative documentation.

(d) Comparison of the antemortem and postmortem findings.

In 1975 SAMIS proposed for the first time a method whereby antemortem an information carrier would be incorporated in the crown of the tooth for postmortem identification. However, the method is complicated, time-consuming, and requires inter alia a diagnostic X-ray apparatus at the point of the accident to discover the SAMIS identification mark on the corpse.

THE INVENTION

It is an object to make it possible for persons who are neither medically nor dentally qualified to make an almost 100% reliable identification on the basis of the teeth of a victim using only a magnifying glass and taking only about half an hour, no X-ray equipment being necessary.

The teeth are generally recognised as a permanent identification object. Their identifying function can be extended if used as an identification carrier for an embossed identification mark. The method according to the invention is characterised by its simplicity, inexpensiveness and reliability.

According to the present invention, human beings are given identifying marks for the purpose of forensic identification by means of visible markings of a tooth or prosthesis. A hole is drilled into the surface of the crown of a tooth, preferably in an oral surface facing the tongue or gums or in a fixed or removable prosthesis of the person to be marked. An information carrier identifying the person is placed in the hole. A coloured plastic which hardens in place is introduced into and over the hole containing the information carrier.

The invention also includes an apparatus for the alpha-numeric marking of the inserted information carrier.

DETAILED DESCRIPTION

Figure 1:
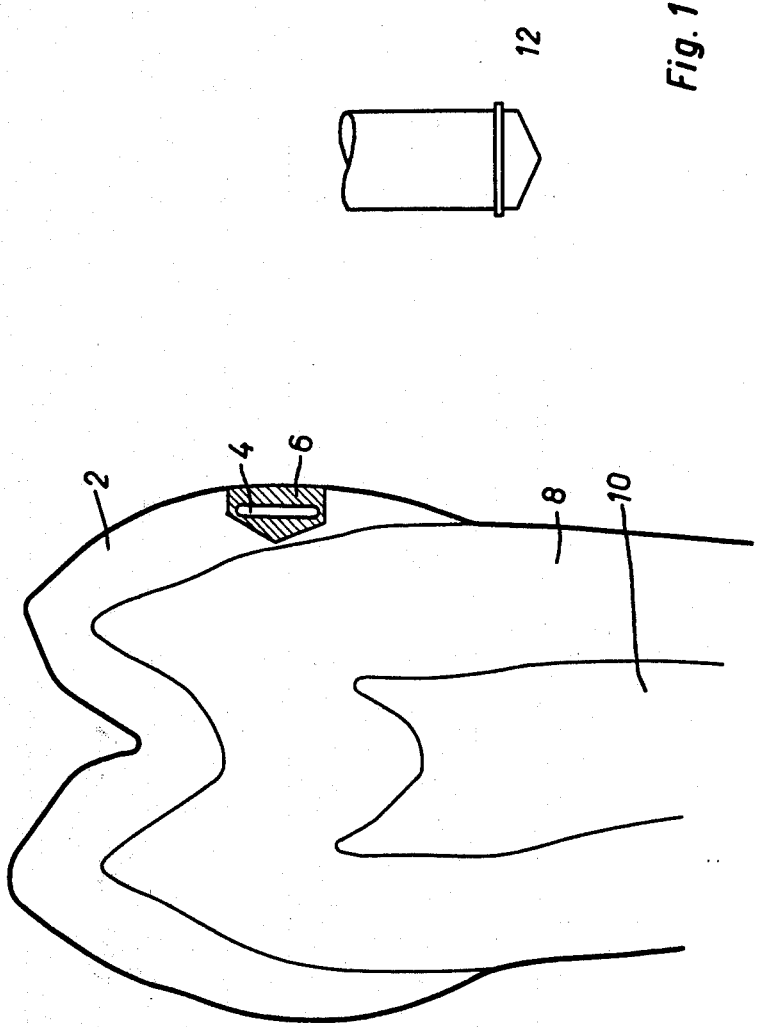
FIG. 1 shows a special drill bit for installation of an information carrier into a tooth in accordance with a preferred embodiment of the present invention and also an outline of such a tooth with the information carrier shown in section.

In a preferred embodiment of the novel method in accordance with the present invention a tooth of a living person is selected as the information carrier. A round cavity is drilled into a crown surface, e.g. the oral crown surface of a molar in the upper or lower jaw. The shape and depth of the cavity are standardised in simple manner by using a standard diamond cutter (FIG. 1). In FIG. 1 are shown the following parts: 2 dental enamel; 4 gold identification plate; 6 filling; 8 dentine; 10 pulp and 12 drill bit.

The cavity has a diameter of approx. 2.0 mm and a depth of approx. 1.0 mm. Prior to insertion of the identification plate in the cavity, its size is checked with a specially constructed dimension probe. The standardized identification plate is placed on the bottom of the cavity and embedded with an adhesive filling material (composite material or the like). By using the acid etching method, a fireproof dye or stain, perferably metal oxides, which subsequently will permit a rapid visual identification of the filling and its location is added to the filling material. The dye or stain should comply with the Bowen formula or other polymer used as the filling material. The color of the filling material can contrast with respect to the color of the surrounding dental crown surface.

Figure 2:
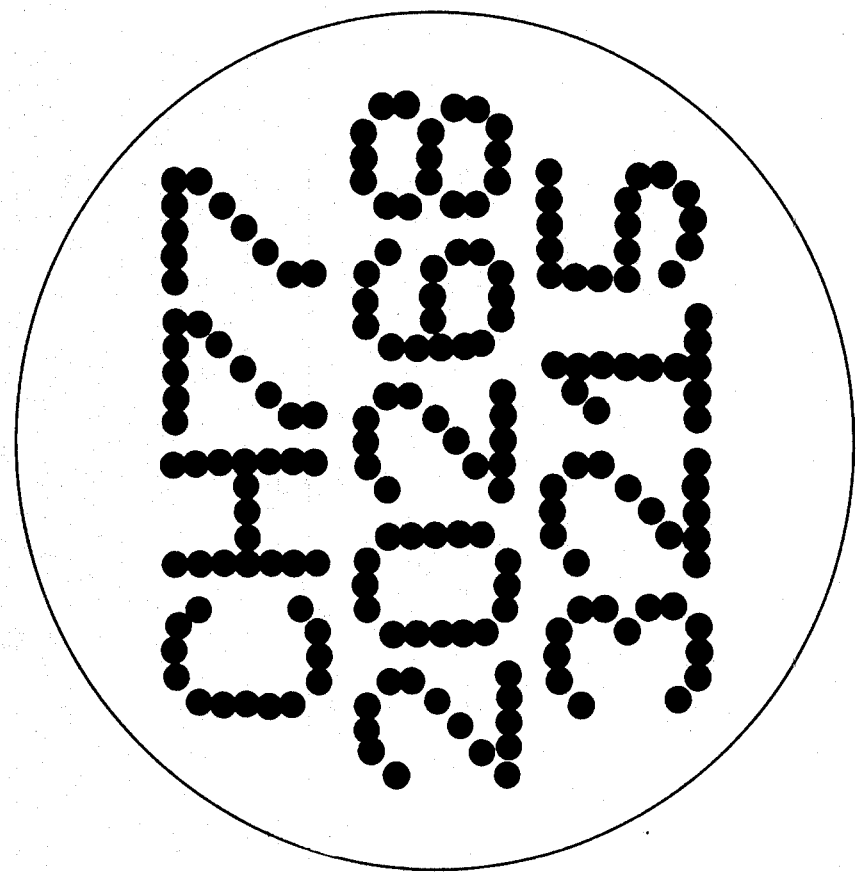
FIG. 2 is a plan view of the information carrier in the tooth of FIG. 1, greatly exaggerated.

The identification plate is preferably a chip of metal, e.g. gold and its alloys. For example, it can be gold with 2% platinum, a plate chip diameter of approximately 2.0 mm a thickness of approximately 0.3 mm, a Vickers hardness of 50, and a melting range of 1,000–1035° C. However, it is also possible to use other embossible materials, such as organic and inorganic polymers, ceramic materials, and the like. Onto the plate is embossed or stamped a number with a sufficiently identifying corresponding National code, such as for the case of a Swiss resident, his old age and surviving dependents insurance number (AHV-No.) (FIG. 2).

Figure 3:
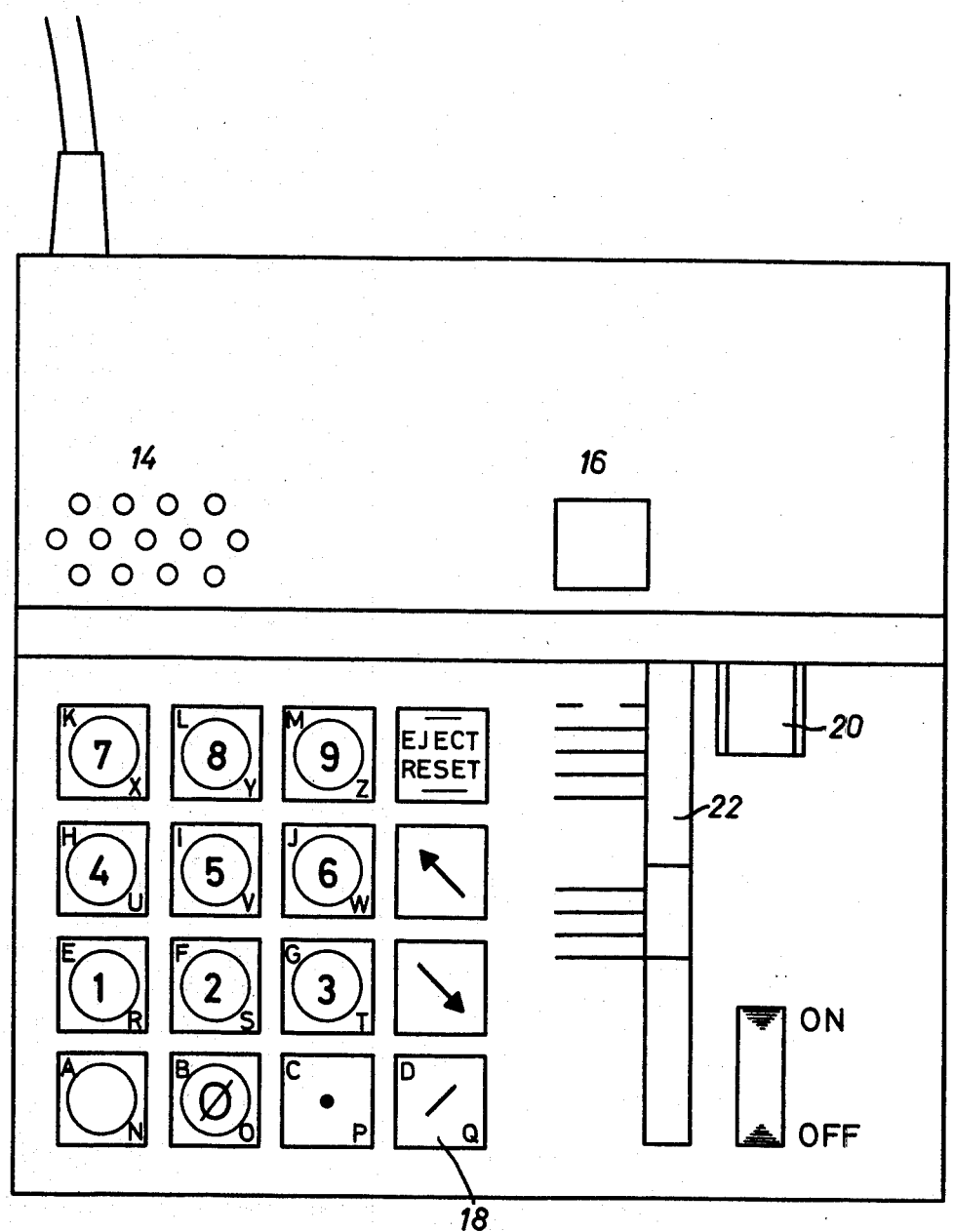
FIG. 3 is a plan view of a preferred embodiment in accordance with the present invention for providing the information on the carrier of FIG. 2.

In order to facilitate the embossing process, and consequently the performance of the present method, there is contemplated an embossing apparatus which is operated by means of a keyboard and which within 2 to 3 minutes is able to produce an identification mark with the desired code (FIG. 3). In FIG. 3 the following are indicated: 14 indicator lamps; 16 checking magnifying glass, 18 keyboard, 20 ejection slot and 22 magazine store.

As soon as the code numbers and letters have been typed, the embossing process starts automatically. A Microprocessor is used for the overall control.

The above-described method permits the identification of a person in a manner which is substantially independent of external circumstances, e.g. the diaster location or situation. The identification mark remains intact despite decomposition or burning of the corpse. It can also be rapidly and reliably found in the identification carrier of the victim.

The insertion and embedding of the identification mark is carried out on the oral side of a molar because this area has been proved by experience to be relatively well protected by the surrounding soft areas, i.e. the tongue and cheek from thermal influences in the case of fires. This selected insertion point for the mark also leads to no esthetic disadvantages. However, depending on the teeth or denture, other crown or denture areas can be used.

The identification mark is inserted during a normal visit to the dentist and the procedure requires no trained specialist. The identification plate can be prepared by any dental assistant or nurse, without special training.

The rediscovery of the identification mark on the corpse takes place by visual detection of the fireproof dye or stain, e.g. red point in a preferably oral crown surface. The particular tooth is extracted or isolated and the adhesive film dissolved with chloroform. To remove the identification mark, it is also possible to fragment the entire tooth in a vise. The red filling comes out, usually with the metal foil and is dissolved with chloroform and cleaned. The code can then be easily read by means of a magnifying glass.

The advantages of the identification according to the invention are:

(a) Identification of the victim without dependence on antemortem comparison material.

(b) The identification mark can be readily non-trained personnel (e.g. it takes 3 minutes).

(c) Preparation and insertion of the identification plate by a dentist into a previously drilled cavity can be done within 5 to 10 minutes.

(d) There is provided clear visual indication of the location of the identification plate in the tooth or prosthesis, preferably on the oral crown surface of the tooth and on the corpse, for non-specialists.

(e) The identification of the corpse is substantially independent of external destructive influences, the resistance or strength of the identification plate being similar to that of the tooth.

(f) The identification plate can be discovered in the oral cavity at the disaster location by personnel without special training.

The term "dental" as used herein is intended to refer to both natural and prosthetic tooth and associated structures which are fixed in the mouth for chewing purposes.

We claim:

1. A method for providing the body of a living person with visually identifiable and locatable permanent identifying information, comprising the steps of:

providing a shallow cavity in the surface of a dental crown in the person's mouth, installing in the shallow cavity an information carrier of durable material, the carrier being provided with information as to the identity of the person, and filling the shallow cavity with a filling material which, on at least the surface of the filling material has a coloring which is visually identifiable with respect to the color of the dental crown surface, said filling material embedding the plate and hardening to a durable, heat resistant filling.

2. The method of claim 1 wherein the providing of a shallow cavity is by drilling a blind hole in an intact dental crown surface of a natural tooth.

3. Method according to claim 1, wherein the color of the filling material is contrasting with respect to the color of the dental crown surface.

4. Method according to claim 1, wherein the step of providing the cavity comprises forming the cavity in an oral surface of the dental crown.

5. Method according to claim 1, wherein the step of installing the information carrier comprises the step of installing a sheet or plate-like carrier of non-corrosive, dentally physiologically compatible material.

6. Method according to claim 5, wherein the material is a gold or gold alloy.

7. Method according to claim 5, wherein the material is an organic polymer.

8. Method according to claim 5, wherein the material is an inorganic polymer.

9. Method according to claim 5, wherein the material is a ceramic.

* * * * *